US011399798B2

(12) United States Patent
Duric et al.

(10) Patent No.: US 11,399,798 B2
(45) Date of Patent: *Aug. 2, 2022

(54) METHOD OF CHARACTERIZING TISSUE OF A PATIENT (71) Applicant: Delphinus Medical Technologies, Inc., Novi, MI (US)

(72) Inventors: Nebojsa Duric, Novi, MI (US); Peter John Littrup, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 903 days.

This patent is subject to a terminal disclaimer.

(21) Appl. No.: 16/217,275

(22) Filed: Dec. 12, 2018

(65) Prior Publication Data
US 2019/0150885 A1    May 23, 2019

Related U.S. Application Data (60) Continuation of application No. 15/731,000, filed on Oct. 12, 2017, now Pat. No. 10,231,696, which is a
(Continued)

(51) Int. Cl.
*A61B 8/08*    (2006.01)
*A61B 8/00*    (2006.01)
(Continued)

(52) U.S. Cl.
CPC ............ *A61B 8/0825* (2013.01); *A61B 8/085* (2013.01); *A61B 8/0833* (2013.01); *A61B 8/406* (2013.01);
(Continued)

(58) Field of Classification Search
None
See application file for complete search history.

(56) References Cited

U.S. PATENT DOCUMENTS 3,154,067 A    10/1964  Stenstrom et al.
3,771,355 A    11/1973  Sachs
(Continued)

FOREIGN PATENT DOCUMENTS

CA    2324602 A1    9/1999
EP    0284055 A2    9/1988
(Continued)

OTHER PUBLICATIONS

Banihashemi, B. et al., "Ultrasound Imaging of Apoptosis in Tumor Response: Novel Preclinical Monitoring of Photodynamic Therapy Effects," Cancer Research, vol. 68, No. 20, Oct. 15, 2008, pp. 8590-8596.
(Continued)

*Primary Examiner* — Katherine L Fernandez
*Assistant Examiner* — Michael S Kellogg
(74) *Attorney, Agent, or Firm* — Wilson Sonsini Goodrich & Rosati (57) ABSTRACT

A method for characterizing tissue of a patient, including receiving acoustic data derived from the interaction between the tissue and the acoustic waves irradiating the tissue; generating a morphology rendering of the tissue from the acoustic data, in which the rendering represents at least one biomechanical property of the tissue; determining a prognostic parameter for a region of interest in the rendering, in which the prognostic parameter incorporates the biomechanical property; and analyzing the prognostic parameter to characterize the region of interest. In some embodiment, the method further includes introducing a contrast agent into the tissue; generating a set of enhanced morphology renderings of the tissue after introducing the contrast agent; determining an enhanced prognostic parameter from the enhanced morphology renderings; and analyzing the enhanced prognostic parameter.

20 Claims, 9 Drawing Sheets

Related U.S. Application Data continuation of application No. 14/755,618, filed on Jun. 30, 2015, now Pat. No. 9,814,441, which is a continuation of application No. 13/711,377, filed on Dec. 11, 2012, now Pat. No. 9,101,290, which is a division of application No. 13/027,070, filed on Feb. 14, 2011, now Pat. No. 8,876,716.

(60) Provisional application No. 61/304,360, filed on Feb. 12, 2010.

(51) Int. Cl.
  *G06T 7/00* (2017.01)
  *A61B 8/06* (2006.01)

(52) U.S. Cl.
  CPC ............ *A61B 8/4494* (2013.01); *A61B 8/461* (2013.01); *A61B 8/466* (2013.01); *A61B 8/469* (2013.01); *A61B 8/481* (2013.01); *A61B 8/483* (2013.01); *A61B 8/5207* (2013.01); *A61B 8/5223* (2013.01); *G06T 7/0014* (2013.01); *A61B 8/06* (2013.01); *G06T 2207/10136* (2013.01); *G06T 2207/30068* (2013.01)

(56) References Cited

U.S. PATENT DOCUMENTS

| | | |
|---|---|---|
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,222,274 A | 9/1980 | Johnson |
| 4,317,369 A | 3/1982 | Johnson |
| 4,328,707 A | 5/1982 | Clement et al. |
| 4,431,008 A | 2/1984 | Wanner et al. |
| 4,433,690 A | 2/1984 | Green et al. |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |
| 4,562,540 A | 12/1985 | Devaney |
| 4,564,019 A | 1/1986 | Miwa |
| 4,646,756 A | 3/1987 | Watmough et al. |
| 4,662,222 A | 5/1987 | Johnson |
| 4,671,256 A | 6/1987 | Lemelson |
| 4,733,562 A | 3/1988 | Saugeon |
| 4,855,911 A | 8/1989 | Lele et al. |
| 4,858,124 A | 8/1989 | Lizzi et al. |
| 4,917,096 A | 4/1990 | Englehart et al. |
| 4,941,474 A | 7/1990 | Pratt, Jr. |
| 5,003,979 A | 4/1991 | Merickel et al. |
| 5,029,476 A | 7/1991 | Metala et al. |
| RE33,672 E | 8/1991 | Miwa |
| 5,095,909 A | 3/1992 | Nakayama et al. |
| 5,103,129 A | 4/1992 | Slayton et al. |
| 5,143,069 A | 9/1992 | Kwon et al. |
| 5,158,071 A | 10/1992 | Umemura et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,268,876 A | 12/1993 | Rachlin |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa, Jr. et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,413,108 A | 5/1995 | Alfano |
| 5,415,164 A | 5/1995 | Faupel et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,513,639 A | 5/1996 | Satomi et al. |
| 5,546,945 A | 8/1996 | Soldner |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,787,049 A | 7/1998 | Bates |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,833,614 A | 11/1998 | Dodd et al. |
| 5,833,627 A | 11/1998 | Shmulewitz et al. |
| 5,846,202 A | 12/1998 | Ramamurthy et al. |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 6,002,958 A | 12/1999 | Godik |
| 6,005,916 A | 12/1999 | Johnson et al. |
| 6,014,473 A | 1/2000 | Hossack et al. |
| 6,023,632 A | 2/2000 | Wilk |
| 6,050,943 A | 4/2000 | Slayton et al. |
| 6,056,690 A | 5/2000 | Roberts |
| 6,083,166 A | 7/2000 | Holdaway et al. |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,149,441 A | 11/2000 | Pellegrino et al. |
| 6,242,472 B1 | 6/2001 | Sekins et al. |
| 6,245,017 B1 | 6/2001 | Hashimoto et al. |
| 6,256,090 B1 | 7/2001 | Chen et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,351,660 B1 | 2/2002 | Burke et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,450,960 B1 | 9/2002 | Rather et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,574,499 B1 | 6/2003 | Dines et al. |
| 6,587,540 B1 | 7/2003 | Johnson et al. |

(56) References Cited

U.S. PATENT DOCUMENTS

| | | |
|---|---|---|
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |
| 6,837,854 B2 | 1/2005 | Moore et al. |
| 6,883,194 B2 | 4/2005 | Corbeil et al. |
| 6,926,672 B2 | 8/2005 | Moore et al. |
| 6,939,301 B2 | 9/2005 | Abdelhak |
| 6,984,210 B2 | 1/2006 | Chambers et al. |
| 7,025,725 B2 | 4/2006 | Dione et al. |
| 7,179,449 B2 | 2/2007 | Lanza et al. |
| 7,285,092 B2 | 10/2007 | Duric et al. |
| 7,346,203 B2 | 3/2008 | Turek et al. |
| 7,497,830 B2 | 3/2009 | Li |
| 7,530,951 B2 | 5/2009 | Fehre et al. |
| 7,556,602 B2 | 7/2009 | Wang et al. |
| 7,570,742 B2 | 8/2009 | Johnson et al. |
| 8,876,716 B2 | 11/2014 | Duric et al. |
| 9,101,290 B2 | 8/2015 | Duric et al. |
| 9,814,441 B2 | 11/2017 | Duric et al. |
| 2001/0029334 A1 | 10/2001 | Graumann et al. |
| 2001/0037075 A1 | 11/2001 | Candy |
| 2002/0065466 A1 | 5/2002 | Rather et al. |
| 2002/0099290 A1 | 7/2002 | Haddad |
| 2002/0131551 A1 | 9/2002 | Johnson et al. |
| 2003/0138053 A1 | 7/2003 | Candy et al. |
| 2004/0030227 A1 | 2/2004 | Littrup et al. |
| 2004/0059265 A1 | 3/2004 | Candy et al. |
| 2004/0152986 A1 | 8/2004 | Fidel et al. |
| 2004/0167396 A1 | 8/2004 | Chambers et al. |
| 2004/0181154 A1 | 9/2004 | Peterson et al. |
| 2005/0165309 A1 | 7/2005 | Varghese et al. |
| 2005/0196025 A1 | 9/2005 | Schofield |
| 2005/0260745 A1 | 11/2005 | Domansky et al. |
| 2006/0009693 A1 | 1/2006 | Hanover et al. |
| 2006/0020205 A1 | 1/2006 | Kamiyama |
| 2006/0064014 A1 | 3/2006 | Falco et al. |
| 2006/0084859 A1 | 4/2006 | Johnson et al. |
| 2006/0085049 A1 | 4/2006 | Cory et al. |
| 2006/0287596 A1 | 12/2006 | Johnson et al. |
| 2006/0293597 A1 | 12/2006 | Johnson et al. |
| 2007/0015949 A1 | 1/2007 | Kaiser |
| 2007/0167823 A1 | 7/2007 | Lee et al. |
| 2008/0045864 A1 | 2/2008 | Candy et al. |
| 2008/0218743 A1 | 9/2008 | Stetten et al. |
| 2008/0229832 A1 | 9/2008 | Huang et al. |
| 2008/0269812 A1 | 10/2008 | Gerber et al. |
| 2008/0275344 A1 | 11/2008 | Glide-Hurst et al. |
| 2008/0281205 A1 | 11/2008 | Naghavi et al. |
| 2008/0294027 A1 | 11/2008 | Frinking et al. |
| 2008/0294043 A1 | 11/2008 | Johnson et al. |
| 2008/0319318 A1 | 12/2008 | Johnson et al. |
| 2009/0035218 A1 | 2/2009 | Ross et al. |
| 2009/0076379 A1 | 3/2009 | Hamill et al. |
| 2009/0129556 A1 | 5/2009 | Ahn et al. |
| 2009/0143674 A1 | 6/2009 | Nields et al. |
| 2010/0331699 A1 | 12/2010 | Yu et al. |
| 2011/0152685 A1 | 6/2011 | Misono |
| 2013/0267850 A1 | 10/2013 | Berman |
| 2014/0316269 A1 | 10/2014 | Zhang et al. |
| 2018/0125447 A1 | 5/2018 | Duric et al. |

FOREIGN PATENT DOCUMENTS

| | | |
|---|---|---|
| EP | 0351610 A2 | 1/1990 |
| EP | 0538241 A2 | 4/1993 |
| EP | 0609922 A2 | 8/1994 |
| EP | 0661029 A1 | 7/1995 |
| EP | 0774276 A2 | 5/1997 |
| EP | 1063920 A1 | 1/2001 |
| JP | 2005253827 A | 9/2005 |
| JP | 2007181679 A | 7/2007 |
| JP | 2009034521 A | 2/2009 |
| WO | WO-9947046 A1 | 9/1999 |
| WO | WO-0228350 A2 | 4/2002 |
| WO | WO-0230288 A1 | 4/2002 |
| WO | WO-2004061743 A2 | 7/2004 |
| WO | WO-2005057467 A2 | 6/2005 |
| WO | WO-2007023408 A2 | 3/2007 |
| WO | WO-2011100697 A1 | 8/2011 |

OTHER PUBLICATIONS

Boone et al., "Dedicated Breast CT: Radiation Dose and Image Quality Evaluation," Med Phys 221(3): 657-667, (2001).

Boston et al., "Estimation of the Content of Fat and Parenchyma in Breast Tissue Using MRI T1 Histograms and Phantoms," MRI 23: 591-599, (2005).

Boyd, "Quantitative Classification of Mammographic Densities and Breast Cancer Risk: Results from the Canadian National Breast Screening Study," J Nat'l Cancer Institute, 87(9): 670-675, (1995).

Byng et al., The Quantitative Analysis of Mammographic Densities,: Phys Med Biol 39 (1994), 1629-1638.

"Centerline, PortalVision section, Summer 2002 edition, published by Varian Medical Systems".

Chan et al., An Agglomeration Multigrid Method for Unstructured Grids, Contemporary Mathematics, vol. 218, 1998.

Chang et al., "Breast Density Analysis in 3-D Whole Breast Ultrasound Images," IEEE Proc 28th IEEE EMBS Annual International Conference, (2006), 2795-2798.

Chang et al., Kirchhoff migration of ultrasonic images, Materials evaluation, V59, N3, 413-417, 2001.

Chelfouh et al., "Characterization of Urinary Calculi: in Vitro Study of 'Twin king Artifact' revealed by Color-Flow Sonography," AJR Am. J. Roentgenol., 171(4), (1998), 1055-60.

Chen et al., "Projecting Absolute Invasive Breast Cancer Risk in White Women with a Model that Includes Mammographic Density," J. Nat'l Cancer Institute, 98(17), (2006), 1215-1226.

Diederich et al., "The design of ultrasound applicators for interstitial hyperthermia," Ultrasonics Symposium, Proc IEEE 1993 Baltimore, MD, USA, Oct. 31-Nov. 3, 1993, New York, NY, USA, 1215-1219.

Duric et al., "Computed Ultrasound Risk Evaluation," Barbara Ann Karmanos Cancer Institute, pp. 1-23, 2008.

Duric et al., "Detection of Breast Cancer with Ultrasound Tomography: First Results with the Computed Ultrasound Risk Evaluation (CURE) Prototype," Med Phys, 34(2), (2007).

Dussik, "The Ultrasonic Field as a Medical Tool," Amer J Phys Med, 33(1), (1954), 5-20.

European search report dated Jul. 6, 2017 for EP Application No. 11742970.4.

Fjield et al.. "A Parametric Study of the Concentric-Ring Transducer Design for MRI Guided Ultrasound Surgery," J. Acoust. Soc. America, 100 (2), Pt. 1 (1996).

Gervias et al., "Renal Cell Carcinoma: Clinical Experience and Technical Success with Radio-frequency Ablation of 42 Tumors," Radiology, 226, (2003), 417-424.

Glide, "A Novel Approach to Evaluating Breast Density Using Ultrasound Tomography," Dissertation Graduate School of Wayne State University (2007).

Glide et al., "Novel Approach to Evaluating Breast Density Utilizing Ultrasound Tomography," Med Phys, 34(2), (2007), 744-753.

Glide-Hurst, "A New Method for Quantitative Analysis of Mammographic Density," Med Phys, 34(11), (2007), 4491-4498.

Glide-Hurst et al., "A Novel Ultrasonic Method for Measuring Breast Density and Breast Cancer Risk," Med Imaging 2008, Proc SPIE, vol. 6920, 69200Q.

Glide-Hurst et al., "Volumetric breast density evaluation from ultrasound tomography images", Medical Physics, vol. 35, 2008, pp. 3988-3997.

Greenleaf, "Computerized Tomography with Ultrasound," Proc IEEE, 71(3), (1983), 330-337.

(56) References Cited

OTHER PUBLICATIONS

Greenleaf, et al. Artificial Cavitation Nuclei Significantly Enhance Acoustically Incuded Cell Transfection. Ultrasound Med & Biol, 24, (1998), 587-595.
Hayashi, "A New Method of Measuring in Vivo Sound Speed in the Reflection Mode," J Clin Ultrasound, 16(2), (1988), 87-93.
International search report and written opinion dated May 20, 2011 for PCT Application No. PCT/US2011/024773.
Jellins et al., "Velocity Compensation in Water-Coupled Breast Echography," Ultrasonics 11(5), (1973), 223-6.
Kaizer et al., "Ultrasonographically Defined Parenchymal Pattenrs of the Breast: Relationship to Mammographic Patterns and Other Risk Factors for Breast Cancer," Brit J Radiology 61(722) (1988) 118-24.
Karssemeijer. "Automated Classification of Parenchymal Patterns in Mammograms," Phys Med Biol, 43, (1998), 365-378.
Kerlikowske et al., "Longitudinal Measurement of Clinical Mammographic Breast Density to Improve Estimation Breast Cancer Risk," J. Nat'l Cancer Institute, 99(5), (2007), 386-395.
Klimes, et al., Grid Travel-time Tracing: Second-order Method for the First Arrivals in Smooth Media, PAGEOPH, 1996, 148:539-63.
Kossoff et al., "Average Velocity of Ultrasound in the Human Female Breast," J Acoust Soc America, 53(6), (1973), 1730-6.
Li et al., Breast Imaging Using Transmission Ultrasound: Reconstructing Tissue Parameters of Sound Speed and Attenuation, 2008 International Conference on BioMedical Engineering and Informatics, IEEE Computer Society, 708-712.
Li et al., Comparison of Ultrasound Attenuation Tomography Methods for Breast Imaging, Medical Imaging 2008: Ultrasonic Imaging and Signal Processing, Proc. of SPIE., vol. 6920, 692015-(1-9), 2008.
Li et al., "In Vivo Breast Sound-Speed Imaging with Ultrasound Tomography", Ultrasound in Med & Bioi., vol. 35, No. 10, 2009, pp. 1615-1628.
Li et al., Refraction Corrected Transmission Ultrasound Computed Tomography for Application in Breast Imaging, Med. Phys. 37(5), May 2010, 2233-2246.
Li et al., "Clinical Breast Imaging Using Sound-Speed Reconstructions of Ultrasound Tomography Data," Med Imaging 2008, Proc SPIE, vol. 6920, 6920009.
Louvar et al., "Correlation of Color Doppler Flow in the Prostate with Tissue Microvascularity," Cancer 1 :83(1), (1998), 135-40.
Marias, "Automatic Labelling and BI-RADS Characterisation of Mammogram Densities," Proc 2005 IEEE, Sep. 1-4, 2005, pp. 6394-6398.
Mast, "Empirical Relationships Between Acoustic Parameters in Human Soft Tissues," Acoust Research Letters Online, Nov. 16, 2000, pp. 37-42.
Masugata et al., "Relationship Between Myocardial Tissue Density Measured by Microgravimetry and Sound Speed Measured by Acoustic Microscopy," Ultrasound in Med & Biol, 25(9), (1999), 1459-1463.
McCormick et al., Multigrid Solution of a Linearized, regularized least-squares problem in electrical impedance tomography, Inverse Problems 9, 1993, 697-713.
Metz, "Basic Principles of ROC Analysis"; Semin Nucl Med., Oct. 8, 1978 (4):283-98.
Metz, "Receiver Operating Characteristic Analysis: A Tool for the Quantitative Evaluation of Observer Performance and Imaging Systems," J Am Coli Radiol 2006; 3: 413-422.
Metz, "Roc Methodology in Radiologic Imaging"; Invest Radiol., Sep. 21, 1986, (9):720-33.
Miller et al., "Sonoporation of Cultured Cells in the Rotating Tube Exposure System," Ultrasound Med & Biol, 25 (1999), 143-149.
Noble et al., "Spleen Hemostasis Using High-Intensity Ultrasound: Survival and Healing," J. Trauma Injury, Infection, and Critical Care, 53(6), (2002), 1115-1120.

Notice of allowance dated May 8, 2015 for U.S. Appl. No. 13/711,377.
Notice of allowance dated Jul. 12, 2017 for U.S. Appl. No. 14/755,618.
Notice of allowance dated Aug. 12, 2014 for U.S. Appl. No. 13/027,070.
Office action dated Feb. 8, 2013 for U.S. Appl. No. 13/027,070.
Office action dated Aug. 17, 2012 for U.S. Appl. No. 13/027,070.
Office action dated Sep. 12, 2014 for U.S. Appl. No. 13/711,377.
Office action dated Nov. 21, 2013 for U.S. Appl. No. 13/027,070.
Oh et al., Multigrid Tomographic Inversion with Variable Resolution Data and Image Spaces, IEEE Transactions on Image Proessing, vol. 15, No. 9, Sep. 2006.
Ophir et al., "Eiastography: Ultrasonic Estimation and Imaging of the Elastic Properties of Tissues," Proc Instn Meeh Engrs, 213(Part H), (1999), 203-233.
Orden, et al. Kinetics of a US Contrast Agent in Benign and Malignant Adnexal Tumors; pub. Radiology 2003; 226:405-410.
Palomares et al., "Mammographic Density Correlation with Gail Model Breast Cancer Risk Estimates and Component Risk Factors," Cancer Epidemiol Biomarkers Prev, 15(7), (2006), 1324-1330.
Quan et al., Sound-speed Tomography using First-arrival Transmission Ultrasound fora Ring Array, Medical Imaging 2007: Ultrasonic Imaging and Signal Processing, Proc. of SPIE, vol. 6513.
Robinson et al., "Quantitative Sonography," Ultrasound in Med & Biol, 12(7): 555-65, (1986).
Saracco, Ariel. Contrast Enhanced Ultrasound (Ceus) in Breast Tumors; pub Division of Medical Imaging and Technology, Department of Clinical Science, Intervention and Technology (CLINTEC) Karolinska Institutet, Stockholm, Sweden 2013.
Sehgal, et al. Delta projection imaging on contrast-enhanced ultrasound to quantify tumor microvasculature and perfusion; pub. Acad Radiol. Jan. 2009; 16(1): 71-78.
Singh, Seema et al., "Color Doppler Ultrasound as an Objective Assessment Tool for Chemotherapeutic in Response Advanced Breast Cancer," Breast Cancer, 2005, vol. 12, No. 1, 2005, pp. 45-51.
Teubner et al., "Comparative Studies of Various Echomammography," Ultraschall in Der Medizin, 3(3) (1982), 109-18, Thieme Verlag, Stuttgart/New York.
Vaezy et al., "Real-Time Visualization of High-Intensity Focused Ultrasound Treatment Using Ultrasound Imaging," Ultrasound in Med & Biol, 27(1), (2001), 33-42.
Walach et al., Local Tissue Attenuation Images Based on Pulsed-Echo Ultrasound Scans, IEEE Transactions on Biomedical Engineering, vol. 36. No. 2, Feb. 1989.
Wei et al., "Correlation Between Mammographic Density and Volumetric Fibroglandular Tissue Estimated on Breast MR Images," Med Phys, 31(4), (2004), 933-942.
Weiwad et al., "Direct Measurement of Sound Velocity in Various Specimens of Breast Tissue," Invest Radiol, 35(12), (2000), 721-6.
Wolfe, "Risk for Breast Cancer Development Determined by Mammographic Parenchymal Pattern," Cancer, 37(5), (1976), 2486-2493.
Xu, et al., "A Study of 3-Way Image Fusion for Characterizing Acoustic Properties of Breast Tissue," Medical Imaging 2008: Ultrasonic Imaging and Signal Processing, Feb. 16, 2008.
Yaffe, "Breast Cancer Risk and Measured Mammographic Density," Eur J Cancer Prevention, 7(1), (1998), S47-55.
Yaman, C et al., "Three-Dimensional Ultrasound to Assess the Response to Treatment in Gynecological Malignancies," Gynecologic Oncology, Academic Press, vol. 97, No. 2, May 1, 2005, pp. 665-668.
Yankelevitz et al., "Small Pulmonary Nodules: Volumetrically Determined Growth Rates Based on CT Evaluation," Radiology, 217, (2000), 251-256.
Zhang et al., A Comparison of Material Classification Techniques for Ultrasound Inverse Imaging, J. Acoust. Soc. Am., 111 (1), Pt. 1, Jan. 2002.

*Examples of enhanced prognostic parameters*

| | Acoustic reflection | Acoustic attenuation | Acoustic speed |
|---|---|---|---|
| S262 | Kinetics | Kinetics | Kinetics |
| S264 | | $\Delta A$ (maximum change) | $\Delta S$ (maximum change) |
| S266 | | $A + \Delta A$ (maximum value) | $S + \Delta S$ (maximum value) |

FIG. 9

METHOD OF CHARACTERIZING TISSUE OF A PATIENT

CROSS-REFERENCE TO RELATED APPLICATIONS

This application is a continuation of prior U.S. application Ser. No. 15/731,000 filed on 12 Oct. 2017, which is a continuation of prior U.S. application Ser. No. 14/755,618 filed 30 Jun. 2015 now U.S. Pat. No. 9,814,441, which is a continuation of prior U.S. application Ser. No. 13/711,377 filed 11 Dec. 2012 now U.S. Pat. No. 9,101,290, which is a divisional of prior U.S. application Ser. No. 13/027,070 filed on 14 Feb. 2011 now U.S. Pat. No. 8,876,716, which claims the benefit of U.S. Provisional Application No. 61/304,360, filed 12 Feb. 2010, each of which is incorporated in their entirety by this reference.

TECHNICAL FIELD

This invention relates generally to the medical imaging field, and more specifically to an improved method of characterizing tissue of a patient in the ultrasound imaging field.

BACKGROUND

Early detection of breast cancer and other types of cancer is typically an important factor to successfully treat cancer. However, there are several reasons that, for some cancer patients, the disease is not detected early. One reason is limitations in the performance of screening. For example, women with dense breast tissue have a very high relative risk for developing breast cancer, but mammography (the current standard tool for breast screening) has low sensitivity for detection of cancer in patients with dense breast tissue, which leads to a relatively high false negative rate. In other words, the performance of mammography is typically worse for this high-risk group of women with dense breast tissue. Another reason contributing to later detection of breast cancer is limited participation in breast tissue screening. Lower participation rates in annual mammograms are partly due to limited access to the screening tool (mammograms require specialized medical centers and highly trained staff), fear of radiation, and discomfort. Furthermore, due to the ionizing nature of mammography, the use of mammography is limited in younger women, who would otherwise be at risk of excessive radiation over their lifetime.

Although magnetic resonance imaging (MRI) improves on some of the limitations of mammography by providing relatively comfortable, radiation-free imaging capability, MRI is prohibitively expensive for routine use and also has limited accessibility. Improved detection of cancer would decrease the percentage of breast cancer incidence at later stages. Thus, there is a need in the medical imaging field to create an improved method of characterizing tissue in a patient. This invention provides such an improved method.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
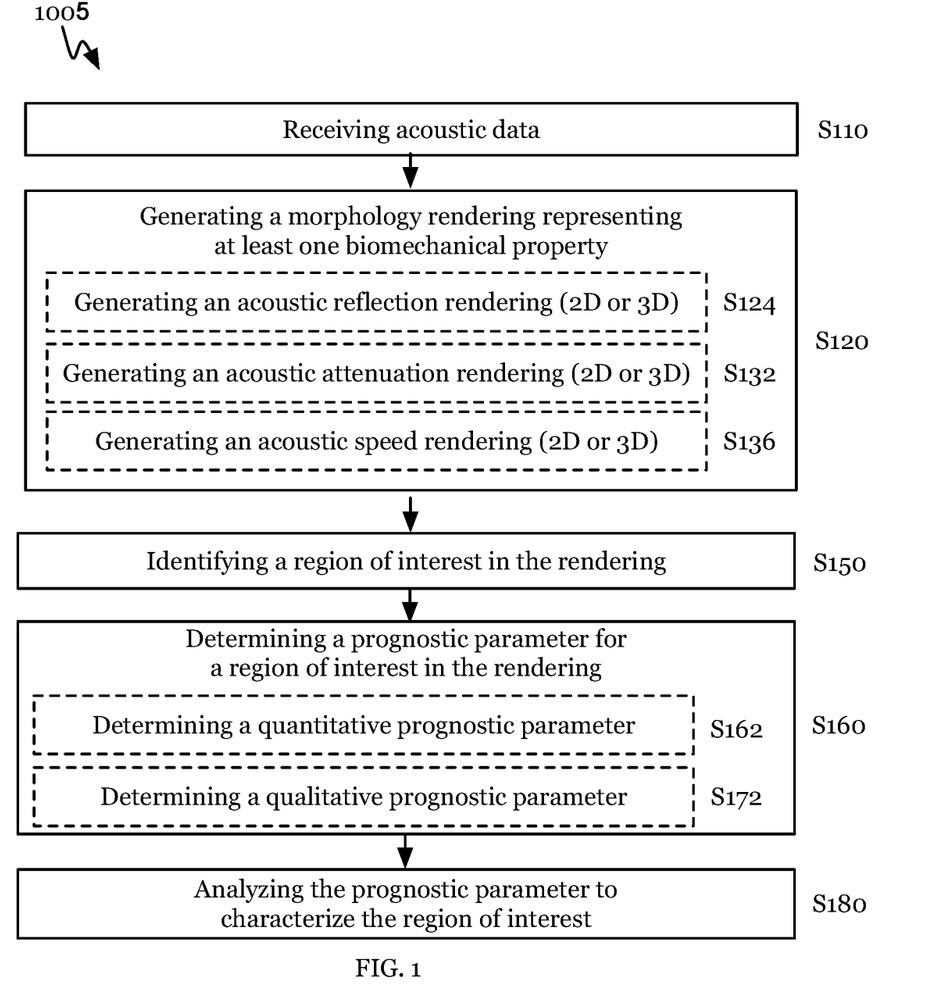
FIG. 1 is a schematic of the method of a first preferred embodiment.

As shown in FIG. 1, the method 100 of characterizing tissue of a patient of a preferred embodiment includes the steps of: receiving acoustic data S110 derived from the interaction between the tissue and the acoustic waves irradiating the tissue; generating a morphology rendering from the acoustic data S120, wherein the rendering represents at least one biomechanical property of the tissue; determining a prognostic parameter for a region of interest in the rendering S160, wherein the prognostic parameter incorporates the biomechanical property; and analyzing the prognostic parameter to characterize the region of interest S180. In a second preferred embodiment, the method further includes the steps of introducing a contrast agent S190. The method enables accurate, inexpensive, comfortable and accessible assessment of a volume of tissue within a patient. The method preferably incorporates ultrasound radiation to obtain acoustic data providing measurements of biomechanical properties of the tissue, such as acoustic reflectivity (based on the reflection of acoustic waves from the tissue), acoustic attenuation (based on amplitude changes of acoustic waves in the tissue), and acoustic speed (based on departure and arrival times of acoustic signals between emitters and receives). In one preferred embodiment, the method is used to detect breast cancer in a human or other animal, but may alternatively be used to detect any suitable kind of cancer. The method may also be used to characterize the tissue to diagnose presence of cancer, assess its type and determine its extent (e.g., to determine whether a malignant mass in the tissue is surgically removable), or to assess risk of cancer development (e.g., measuring breast tissue density). The method may be repeated in different examinations of the patient, such as to allow repeated assessments and tissue characterization of the tissue. For example, repeating the method at various times may facilitate the identification and/or monitoring of a growing lesion (e.g., cancer or fibroadenoma) marked by differences in characterization of the tissue between examinations. The method may, however, be used in any suitable application involving characterization of tissue.

Figure 2A:
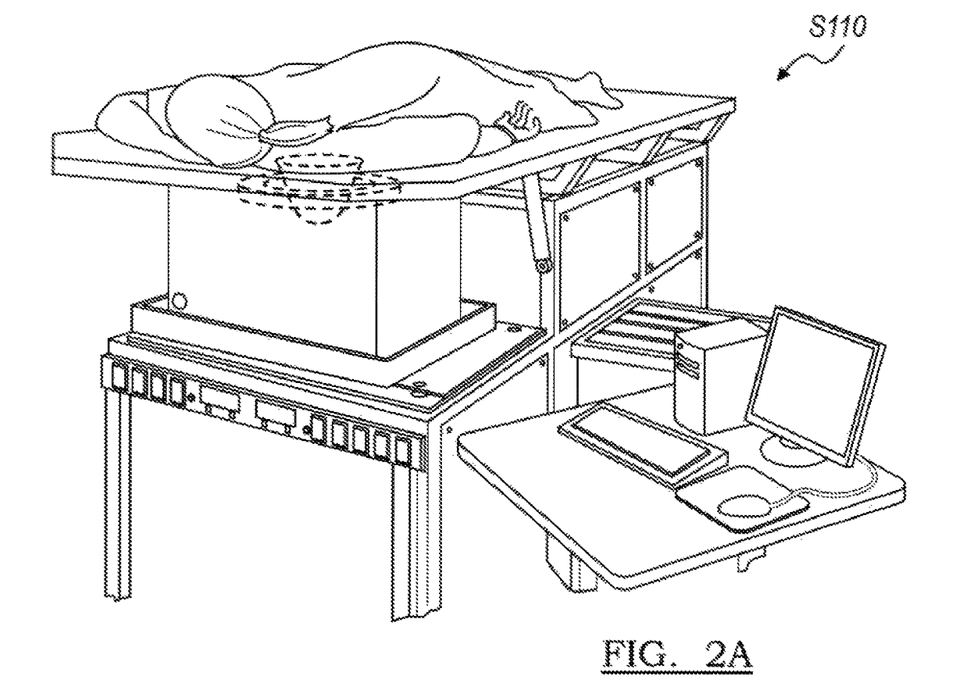
FIG. 2A and FIG. 2B are schematics of an ultrasound scanner used in the method of a preferred embodiment.
Figure 2B:
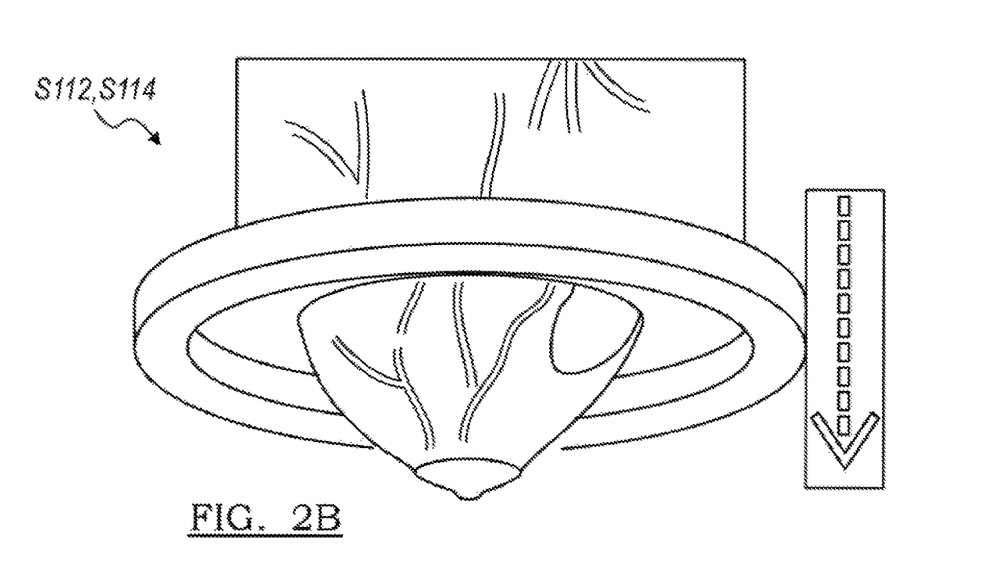

The step of receiving acoustic data S110 functions to irradiate or insonify the tissue in order to obtain acoustic measurement of the tissue. The step of receiving acoustic data S110 preferably includes scanning the tissue S112 with a plurality of transmitters that emit acoustic waves towards the tissue and detecting acoustic waves S114 with a plurality of receivers that detect acoustic waves after the acoustic waves interact with the tissue. The detected acoustic waves preferably include acoustic waves scattered by the tissue, where the scattered acoustic waves includes a mix of reflected and acoustic waves. The steps of scanning the tissue S112 and detecting acoustic waves S114 are preferably performed with an ultrasound tomographic scanner and methods similar to those described in U.S. Pat. Nos. 6,385,474 and 6,728,567, and U.S. Patent Publication Number 2008/0275344, which are incorporated in their entirety by this reference. However, any suitable scanner may be used. As shown in FIG. 2A, the steps of scanning the tissue S112 and detecting acoustic waves S114 are preferably performed during a scan of a patient who lies prone on their stomach on a scanner table having a hole. The table, which may be made of a durable, flexible material such as sailcloth, preferably contours to the patient's body, thereby increasing scanning access to the axilla regions of the breast and increasing patient comfort. The hole in the table allows the breast to protrude through the table and be submerged in an imaging tank filled with water or another suitable fluid to propagate acoustic waves. As shown in FIG. 2B, a ring-shaped transducer is located within the imaging tank and encircles or otherwise surrounds the breast. Multiple emitters that direct safe, non-ionizing ultrasound pulses toward the tissue, and multiple detectors that receive and record data scattering from the tissue, are distributed around the ring transducer. During the scanning step S112, the ring transducer passes along the tissue, such as in an anterior-posterior direction between the chest wall and the nipple region of the breast to acquire an acoustic data set including measurements of acoustic reflection, acoustic attenuation, and acoustic speed, preferably at discrete scanning steps, or coronal "slices". The acoustic data for each "slice" cross-section of the tissue preferably includes an acoustic reflection data set, an acoustic attenuation data set, and an acoustic speed data set. However, the ring transducer may additionally and/or alternatively include any suitable biomechanical property of the tissue during the scanning step. The scanning and detecting steps are preferably quick, such as with a data acquisition time of less than approximately 1 second per "slice", which helps to avoid motion artifacts in the subsequent morphology renderings and enables the use of contrast agents. The step of receiving acoustic data S110 may additionally and/or alternatively include retrieving acoustic data from a storage device such as a hard drive or an online server.

Figure 3A:
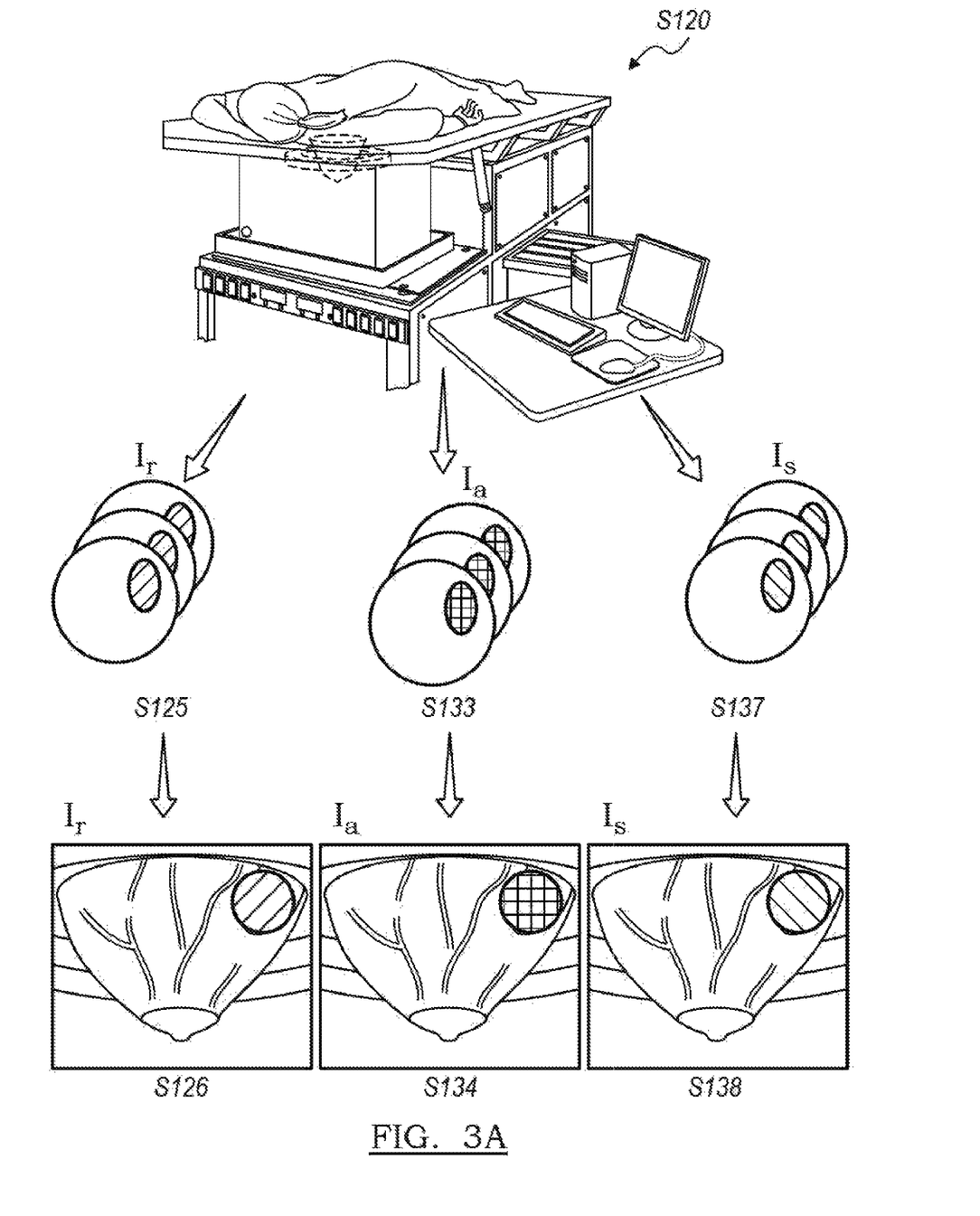
FIG. 3A, FIG. 3B, FIG. 4, FIG. 5A, FIG. 5B, and FIG. 5C are schematics of variations of the step of generating a morphology rendering in the method of a preferred embodiment.
Figure 3B:
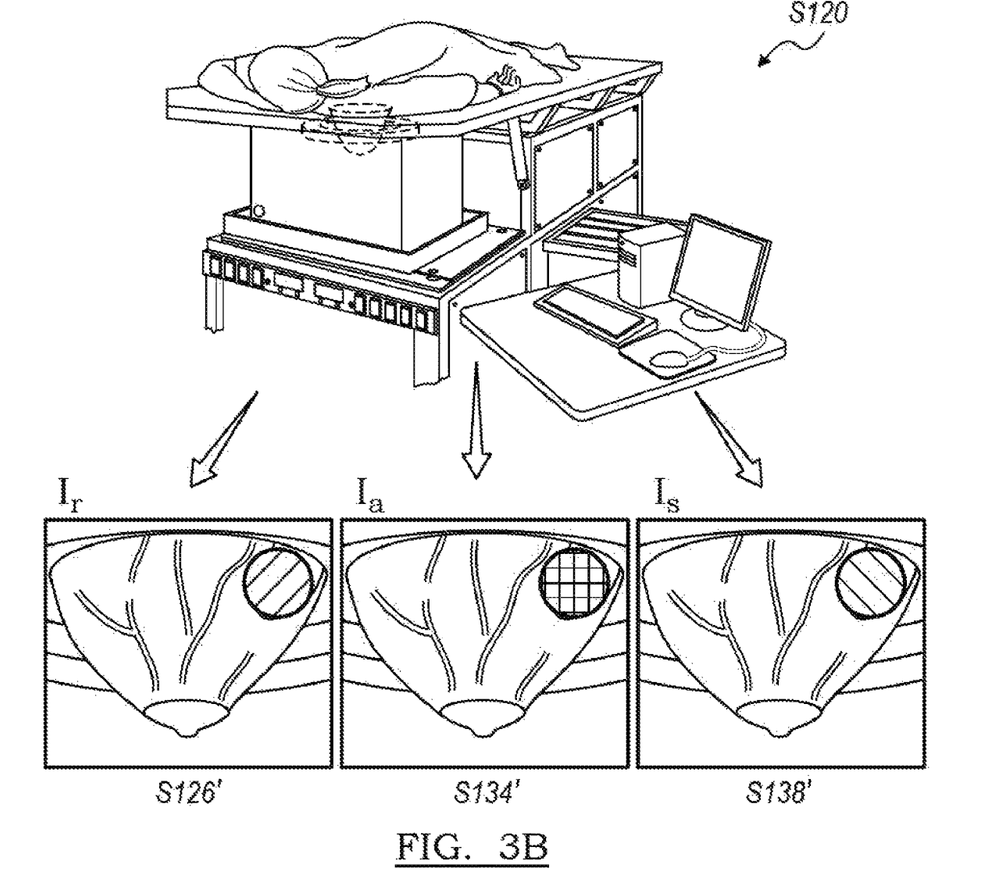

The step of generating a morphology rendering of the tissue from the acoustic data S120 functions to translate the acoustic data into a medium useful for analysis. As shown in FIG. 3A and FIG. 3B, generating a morphology rendering S120 preferably includes generating a plurality of renderings. Each rendering preferably represents a respective biomechanical property of the tissue. As shown in FIG. 1, in a preferred embodiment, generating a plurality of renderings S120 includes generating an acoustic reflection rendering S124 that represents acoustic reflection from the tissue, generating an acoustic attenuation rendering S132 that represents acoustic attenuation within the tissue, and generating an acoustic speed rendering S136 that represents acoustic speed within the tissue. However, generating a plurality of renderings may additionally and/or alternatively include generating any rendering that represents any measurable biomechanical property of the tissue.

As shown in FIG. 3A, generating an acoustic reflection rendering S124 includes generating a set of two-dimensional (2D) images representing acoustic reflection S125, where each image represents acoustic reflection of the tissue at a particular cross-section of the tissue taken during a particular discrete scanning step. In other words, the set of 2D acoustic reflection images forms a stack of 2D renderings that collectively represents acoustic reflection from the entire (or partial) volume of scanned tissue. The set of 2D acoustic reflection images (Ir) is derived from changes in acoustic impedance of the tissue and provides echo-texture data and anatomical detail for the tissue. Generating an acoustic reflection rendering S124 may additionally and/or alternatively include generating a three-dimensional (3D) acoustic reflection rendering S126 that is a volumetric representation of the acoustic reflectivity of the volume of tissue. In a first variation, as shown in FIG. 3A, generating a 3D acoustic reflection rendering S126 includes combining the set of 2D acoustic reflection images into a three-dimensional (3D) acoustic reflection rendering. In a second variation, as shown in FIG. 3B, generating a 3D acoustic reflection rendering S126' includes converting 3D volumetric acoustic data, obtained by scanning the tissue in a 3D manner, directly into a 3D acoustic reflection rendering.

Similar to step S124, generating an acoustic attenuation rendering S132 includes generating a set of 2D images representing acoustic attenuation S133, where each image represents acoustic attenuation within the tissue at a particular cross-section of the tissue taken during a particular discrete scanning step, to form a stack of 2D renderings for acoustic attenuation within the tissue. Generating an acoustic attenuation rendering S132 may additionally and/or alternatively include generating a 3D acoustic attenuation rendering S134 that is a volumetric representation of the acoustic attenuation within the volume of scanned tissue, where variations S134 and S134' may be similar to either variation of analogous steps S126 and S126' for acoustic reflection.

Similar to steps S124 and S132, generating an acoustic speed rendering S136 includes generating a set of 2D images representing acoustic speed S137, where each image represents acoustic speed within the tissue, to form a stack of 2D renderings for acoustic speed within the tissue. Generating an acoustic speed rendering S136 may additionally and/or alternatively include generating a 3D acoustic speed rendering S138 that is a volumetric representation of the acoustic speed within the volume of scanned tissue, where variation S138 and S138' h may be similar to either variation of analogous steps S126 and S126' for acoustic reflection.

Figure 4:
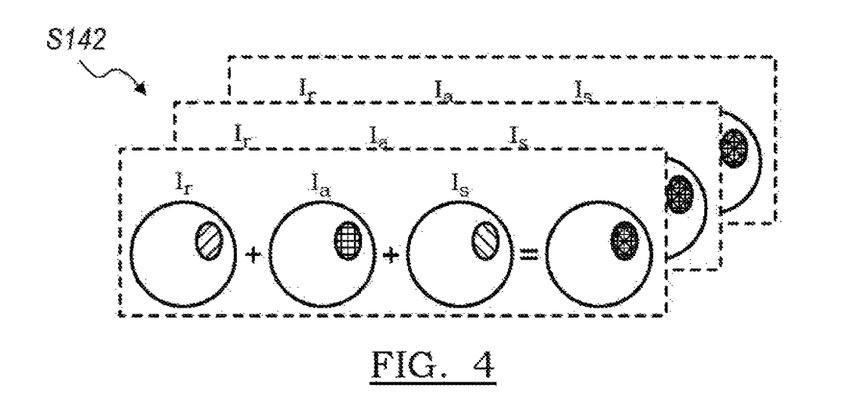
Figure 5A:
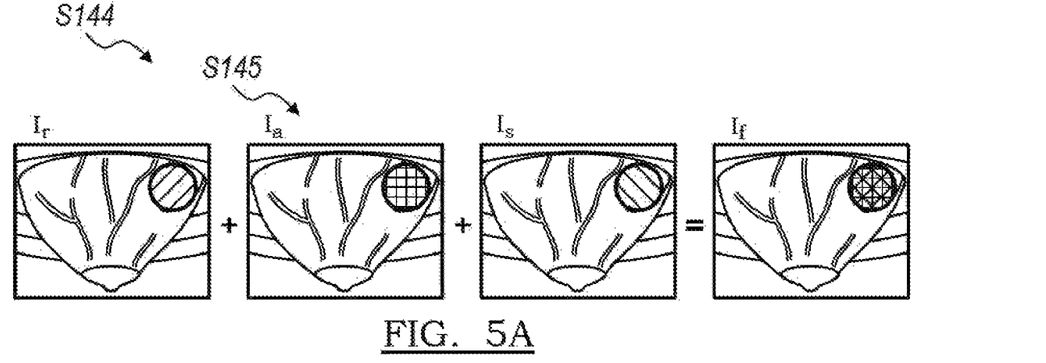
Figure 5B:
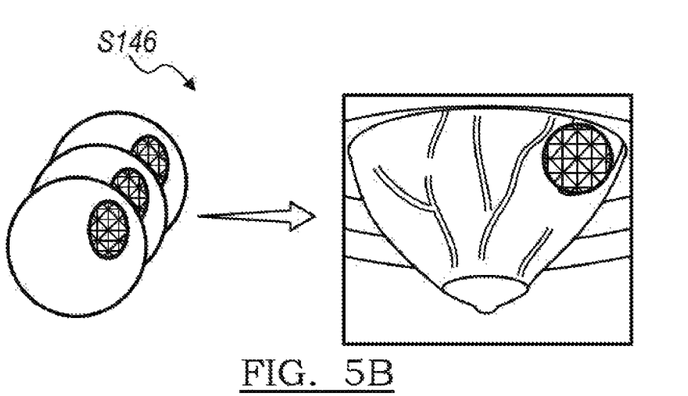

In some embodiments, generating a morphology rendering S120 may further includes combining at least one acoustic reflection rendering, at least one acoustic attenuation rendering, and/or at least one acoustic speed rendering into a set of merged 2D or 3D renderings. In one variation, as shown in FIG. 4, generating a morphology rendering S120 includes generating a set of merged 2D renderings S142 by combining at least a portion of the set of the 2D acoustic reflection renderings, at least a portion of the 2D acoustic attenuation renderings, and/or at least a portion of the 2D acoustic speed renderings. In another variation, generating a morphology rendering S120 includes generating a merged 3D rendering S144. Generating a merged 3D rendering S144 may include combining separate 3D biomechanical property renderings S145 (e.g., combining the 3D acoustic reflection rendering, the 3D acoustic attenuation rendering, and/or the 3D acoustic speed rendering), as shown in FIG. 5A. Generating a merged 3D rendering S144 may alternatively include combining the set of merged 2D renderings into a 3D volumetric rendering S146, as shown in FIG. 5B.

Figure 5C:
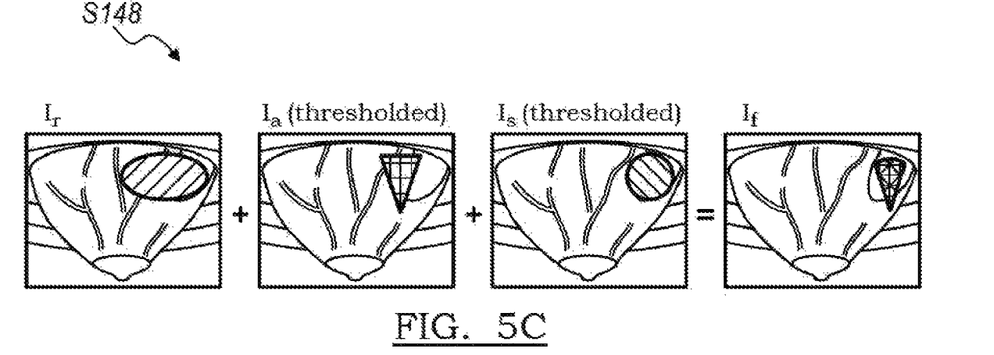

The combined, or merged, renderings are overlaid on one another to allow visualization of multiple biomechanical properties to be viewed simultaneously and facilitate a more comprehensive evaluation of features of the tissue. As shown in FIG. 5C, combining the 2D or 3D renderings into a merged 2D or 3D rendering preferably includes combining the acoustic reflection renderings, a thresholded version of the acoustic attenuation renderings, and a thresholded version of the acoustic speed renderings S148. Variations of the combining step S148 may include combining thresholded (with any suitable threshold values) or non-thresholded versions of any of the renderings. In one embodiment, the renderings are merged by adding: (1) the reflection rendering, (2) a first thresholded version of the acoustic speed rendering (including measurements of the acoustic speed rendering falling between a first speed threshold "a" and a second speed threshold "b") and (3) the combination of a second thresholded version of the acoustic speed rendering (including measurements of the acoustic speed rendering falling above a third speed threshold "c") and a thresholded acoustic attenuation image (including measurements of the acoustic attenuation image above an attenuation threshold). In one embodiment, the thresholds "a", "b", "c", and "d" are set by determining which threshold values yield mass margins (such as the outlines of legions or tissue structures) most similar to those seen in MRI or other relevant imaging modalities. This merging may be expressed according to the formula below, where the bracketed mathematical operation denotes the logical "AND" operation:

$$I_f = I_r + I_s{}_{s=a}^{s=b} + [I_{s>c} \bullet I_{a>d}]$$

However, any suitable formula or algorithm may be used to merge or fuse the various renderings into a single rendering.

The method may further include iterating at least one of the biomechanical property renderings based on the other biomechanical property renderings. For example, altering a threshold used to highlight a region of interest in the acoustic attenuation and/or acoustic speed renderings may change the acoustic attenuation and/or acoustic speed renderings enough to provide additional insight about the nature of the tissue, to iteratively improve the acoustic reflection rendering. However, the iteration may involve revising any of acoustic reflection, acoustic attenuation, and acoustic speed renderings based on any other of the renderings. Furthermore, the method may include iteratively revising thresholds used when merging renderings (e.g., thresholds "a", "b", "c", and "d").

The method may further include the step of identifying a region of interest in the tissue from the morphology rendering S150, which functions to establish a portion of the tissue that requires further attention, such as for diagnosis and/or monitoring purposes. The region of interest, such as a lesion, is preferably identified and/or marked by outlining a mass as it appears on a 3D acoustic reflection rendering. For instance, a threshold of margin sharpness of a suspected mass on the reflection rendering, or another suitable threshold, may be used to identify the boundary of the region of interest in the tissue. The outline of the identified region of interest is preferably replicated on the 3D acoustic attenuation and/or acoustic speed renderings. The region of interest may alternatively be identified as a 2D lesion or mass among the 2D acoustic reflection image renderings and may be replicated on the 2D acoustic attenuation and/or acoustic speed renderings. However, the region of interest may alternatively be identified on the acoustic attenuation and/or acoustic speed renderings, or other biomechanical property rendering. The boundary of the region of interest may be iteratively identified, such as by progressively refining the boundary among the various biomechanical property renderings.

The step of determining a prognostic parameter S160 for a region of interest in the rendering functions to quantify the biomechanical characteristics of the region of interest in the tissue to provide a measure with which to characterize (e.g., to predict, monitor, or otherwise describe) the region of interest. Determining a prognostic parameter may include determining one or more quantitative prognostic parameters S162 and/or one or more qualitative prognostic parameter S172. The quantitative prognostic parameters may involve a reflection index corresponding to the acoustic reflectivity, absolute or relative volume average values of attenuation, and/or absolute or relative volume average values of sound speed of the region of interest. The qualitative prognostic parameters may involve the shape or other characteristics of the acoustic reflection, acoustic attenuation, and acoustic speed of the region of interest in the merged and/or unmerged morphology renderings. Although preferably all of these quantitative and qualitative prognostic parameters are determined, only a portion of these parameters may be determined. In this manner, the prognostic parameters extend beyond the existing Breast Imaging Reporting and Data System BIRADS criteria that are commonly used for 2D ultrasound applications in characterizing tissue masses, by incorporating quantitative measurements of sound speed, attenuation, and/or other biomechanical properties and/or qualitative morphological characteristics of the tissue and/or lesion. These extended prognostic parameters can further extend beyond the current BIRADS criteria into the realm of 3-D characterization by using lesion characterization derived from all three spatial dimensions. Furthermore, additional prognostic information can be gained by characterizing the time dependence of these parameters as derived from multiple patient exams performed at different intervals of time.

Figure 6:
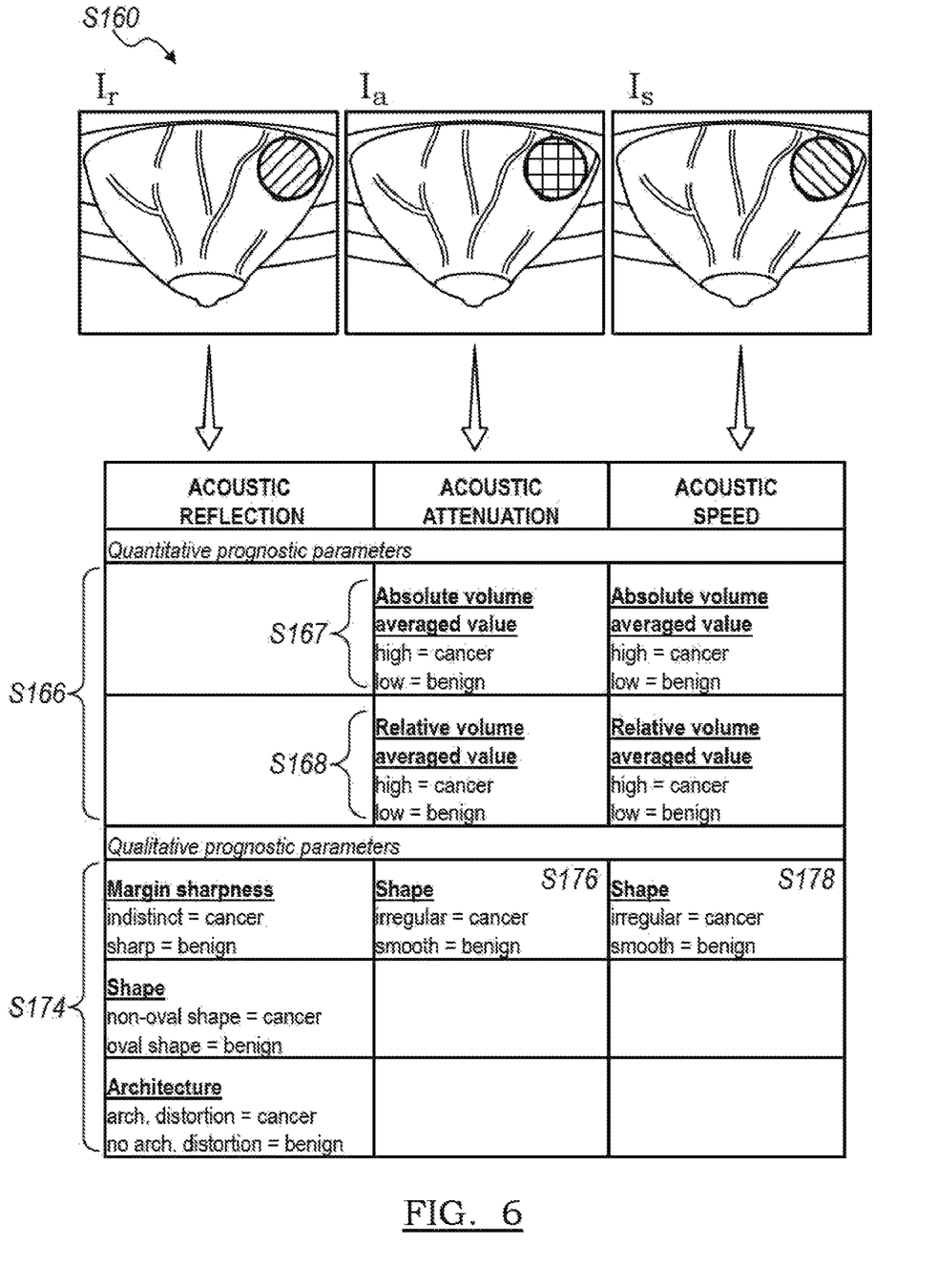
FIG. 6 is a table summarizing the step of determining a prognostic parameter in the method of a preferred embodiment.

As shown in FIG. 6, determining one or more quantitative prognostic parameters S162 may include calculating a volume average value S166 of a biomechanical property of the region of interest from one or more of the renderings. In one variation, calculating a volume average value S166 includes calculating an absolute average (e.g., mean) value of the biomechanical property S167, averaged over the volume of the region of interest. For example, the absolute values of average acoustic attenuation and acoustic speed measurements are preferably calculated from the 3D acoustic attenuation rendering and the 3D acoustic speed rendering, respectively, although they may alternatively be calculated from the 2D acoustic attenuation and acoustic speed renderings, respectively. The absolute values of these averages are preferably determined by statistical analysis of the pixels within the region of interest on the 3D or 2D renderings, and volume-averaged across the mass of the region of interest. However, the volume average may be a representative value of the biomechanical property of the region of interest calculated in any suitable manner. For example, the average value of acoustic speed may be calculated as described in U.S. Patent Publication No. 2008/0275344. As another example, the volume average may additionally and/or alternatively include other aspects, such as being weighted by a spatial distribution of the values of the biomechanical property throughout the region of interest.

In another variation, calculating a volume average value S166 includes calculating a relative value of the biomechanical property S168 that takes into account the difference between the absolute value of the biomechanical property in the region of interest and the value of the biomechanical property in background tissue surrounding the region of interest. Accounting for this difference exploits the measured differences in the biomechanical properties of the region of interest compared to the rest of the scanned tissue. In this variation, calculating a volume average value S166 further includes calculating a background value of the biomechanical property in the tissue outside of the region of interest. In one example, calculating a relative value of the biomechanical property S168 includes subtracting the background value of the biomechanical property from the absolute value of the biomechanical property in the region of interest. Alternatively, calculating a relative value S168 may include dividing the absolute value of the biomechanical property in the region of the interest by the background value of the biomechanical property. However, calculating a relative value of the biomechanical property D168 may include any mathematical operation or other comparison that relates the biomechanical property or properties of the region of interest to that of background tissue. Since any systematic errors from the scan are present in both the background measurements and absolute values of the biomechanical properties, calculating a relative value of the biomechanical property of the region of interest cancels out the systematic errors, and the resulting relative values for the region of interest are thereby normalized. The background value of the biomechanical property is a measurement of the biomechanical property in the background tissue surrounding the region of interest. For example, the background measurement may be the average value of the biomechanical property (e.g., acoustic attenuation or acoustic speed) in a volume of the tissue surrounding the region of interest between the boundary of the region of interest and a surrounding tissue boundary. The surrounding tissue boundary may be defined by extending the boundary of the region of interest by a particular margin, such as 2 centimeters, or any suitable distance. However, the surrounding tissue boundary may be defined in any suitable manner, and the background measurement may be a measurement of the biomechanical property in any suitable portion of the tissue besides the region of interest. In particular, the prognostic parameter may include a relative volume average value of acoustic attenuation for the region of interest, and/or a relative volume average value of acoustic speed for the region of interest.

As shown in FIG. 6, determining one or more qualitative prognostic parameters S172 may include characterizing aspects of the acoustic reflection rendering, the acoustic attenuation rendering and/or the acoustic speed rendering. For the acoustic reflection rendering, determining one or more qualitative prognostic parameters S174 includes characterizing the margin sharpness (e.g., sharp or indistinct), the shape (e.g., oval or not oval), or the architecture (e.g., presence or absence of altered anatomy in surrounding tissue) of the region of interest S174. For the acoustic attenuation rendering, determining one of more qualitative prognostic parameters S172 includes characterizing the 2D or 3D shape (e.g., smooth or irregular) of the region of interest S176 in the acoustic attenuation rendering. For the acoustic speed renderings, determining one of more qualitative prognostic parameters S172 includes characterizing the 2D or 3D shape (e.g., smooth or irregular) of the region of interest S178 in the acoustic speed rendering. However, the qualitative prognostic parameters may characterize any suitable aspect of the biomechanical property renderings. Furthermore, the qualitative prognostic parameters may be converted into a quantitative measure, such as "1" for an indistinct margin and "2" for a sharp margin of the region of interest in the acoustic reflection rendering. As another example, a qualitative prognostic parameter may be converted to a quantitative measure such as a value on a scale (e.g., 1 to 5) that classifies the degree to which the qualitative aspect is expressed. For instance, margin sharpness of the region of interest in the acoustic reflection rendering could be classified with a reflection index as "1" if it very sharp, "3" if it is moderately indistinct, or "5" if it is very indistinct.

The step of analyzing the prognostic parameter S180 functions to utilize the prognostic parameter to predict or otherwise characterize the region of interest. The analysis preferably predicts whether the region of interest is a cancerous mass, a benign fibroadenoma, a cyst, another benign finding, an unidentifiable mass (for example, there is no finding), or any suitable characterization or classification. However, the analysis may additionally and/or alternatively monitor trends of one or more prognostic parameters over time, or for any suitable application. The step of analyzing the prognostic parameter S180 preferably involves the analysis of multiple prognostic parameters, which may be quantitative or qualitative. For example, as shown in FIG. 6, the analysis may evaluate prognostic parameters that may individually suggest the presence of cancer. For parameters regarding acoustic reflection, the signature of a cancerous mass is typically marked in the acoustic reflection image by having an indistinct and/or ill-defined speculated or microlobulated margin, a non-oval shape, and architectural distortion including altered anatomy in surrounding tissue due to mass effect and/or retraction. In contrast, a benign mass is typically marked in the acoustic reflection image by having a sharp margin, an oval shape, and little to no architectural distortion. For parameters regarding acoustic attenuation, the signature of a cancerous mass is typically marked by having relatively high absolute and relative volume averaged values of acoustic attenuation, since acoustic waves typically have higher attenuation within a cancerous mass than within surrounding fatty tissue such as breast tissue. In contrast, a benign mass is typically marked by having relatively low absolute and relative volume averaged values of attenuation. For example, acoustic waves transmitted through a tumor at a frequency of 2 MHz typically experience an attenuation of approximately 0.25 to 0.5 dB/cm relative to fat. For parameters regarding acoustic speed, the signature of a cancerous mass is marked by having relatively high acoustic speed, since acoustic waves typically travel at faster speeds within a cancerous mass than within surrounding fatty tissue such as breast tissue. For example, acoustic waves travel approximately 50-150 meters/second faster in a cancerous mass than in fatty tissue. In contrast, a benign mass is typically marked by having relatively low absolute and relative volume averaged values of acoustic speed.

Figure 7A:
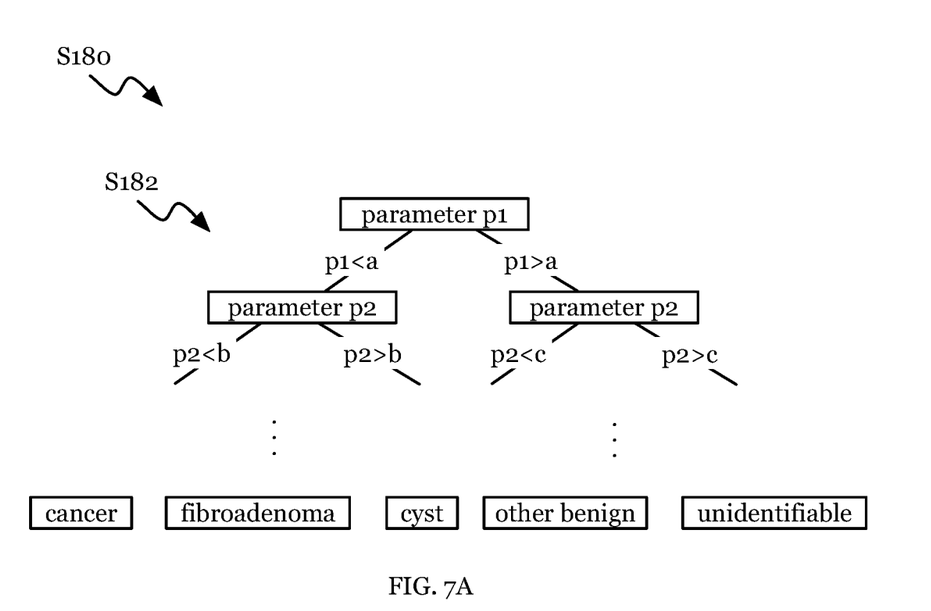
FIG. 7A and FIG. 7B are schematics of a decision tree variation and a predictive model variation, respectively of the step of analyzing the prognostic parameter in the method of a preferred embodiment.

In a first variation, the step of analyzing the prognostic parameter S180 includes navigating a decision tree S182 that compares the prognostic parameters to various thresholds in a branched manner that arrives at a final characterization of the region of interest based on the comparisons between the prognostic parameters to the thresholds. The decision tree preferably incorporates prognostic parameters for acoustic reflection, acoustic attenuation, and/or acoustic speed, but may additionally and/or alternatively incorporate parameters for any suitable biomechanical properties (such as quantitative classifications of qualitative prognostic parameters). In one specific embodiment, a comparison at the "top" of the decision tree branches into a first branch if the absolute or relative volume average acoustic attenuation value is less than or equal to a first threshold, and into a second branch if the absolute or relative volume average attenuation is greater than the threshold. Each of these first and second branches are further divided into different paths based on how the absolute or relative volume averages for reflection index, acoustic attenuation, and acoustic speed compare to other thresholds. By following the decision tree, the prognostic parameters lead to the determination or prediction that the region of interest is, for example, cancerous or not cancerous. The particular thresholds may be determined empirically, such as by comparing the diagnostic results of a set of thresholds to the diagnostic results of other methods such as MM and/or incorporating data and ultrasound tomography from known cancer patients. Furthermore, the importance of each prognostic parameter is preferably evaluated using attribute selection algorithms such as chi-square method, gain ratio, and information gain, which are strategies known to one ordinarily skilled in the art.

Figure 7B:
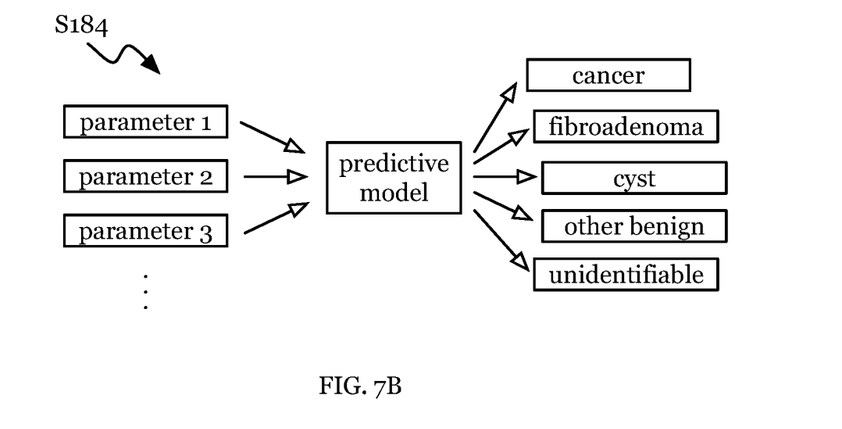

In a second variation, as shown in FIG. 7B, the step of analyzing the prognostic parameter S180 includes inputting the prognostic parameter into a predictive model S184. The input may include prognostic parameters for acoustic reflection, acoustic attenuation, and/or acoustic speed, but may additionally and/or alternatively incorporate parameters for any suitable biomechanical properties (such as quantitative classifications of qualitative prognostic parameters). The prediction model may be externally validated by using data from known cancer patients or other patients with known types of lesions. However, the prediction model may be validated by any suitable process. Furthermore, in creation of the prediction model, the prediction model is preferably evaluated to identify covariate patterns that may be disproportionately influential or systematically associated with misclassification. The evaluation preferably incorporates a receiver operating characteristic (ROC) curve as a tool to select one or more possibly optimal predictive models. The ROC curve is preferably constructed using model estimates to determine the weighted combination of acoustic reflectivity, acoustic attenuation, and acoustic speed that predicts cancer with the lowest false positive rate while maintaining sensitivity of at least 90%. The area under the ROC curve represents the overall accuracy of the mode, summarizing: (1) sensitivity, or the proportion of patients in the data set with cancer who are determined by the scanner as having cancer, (2) specificity, the proportion of patients in the data set without cancer who are determined by the scanner as not having cancer, (3) the false positive rate, or the proportion of patients in the data set without cancer who are incorrectly determined by the scanner as having cancer, and (4) the false negative rate, or the proportion of patients in the data set with cancer who are incorrectly determined by the scanner as not having cancer. The sensitivity and specific are preferably conditional estimates that are conditional on the finding of a suspicious region of interest among the empirical data set. However, other aspects of the ROC curve, and/or other methods, may further be used to develop and evaluate the predictive mode.

In a third variation, the step of analyzing the prognostic parameter S180 includes evaluating qualitative prognostic parameters that individually suggest the presence of cancer. For parameters regarding acoustic reflection, the signature of cancerous tissue is typically marked in the acoustic reflection image by having (1) an indistinct and/or ill-defined speculated or microlobulated margin, (2) a non-oval shape, and (3) architectural distortion including altered anatomy in surrounding tissue due to mass effect and/or retraction. In contrast, a benign mass is typically marked in the acoustic reflection image by having (1) a sharp margin, (2) an oval shape, and (3) little to no architectural distortion.

Other variations of analyzing the prognostic parameter S180 may include various suitable combinations of the first, second, and third variations. For instance, two or all three of the variations may be performed, and the outcome of the analysis may be the characterization that the majority of the variations produce.

Figure 8A:
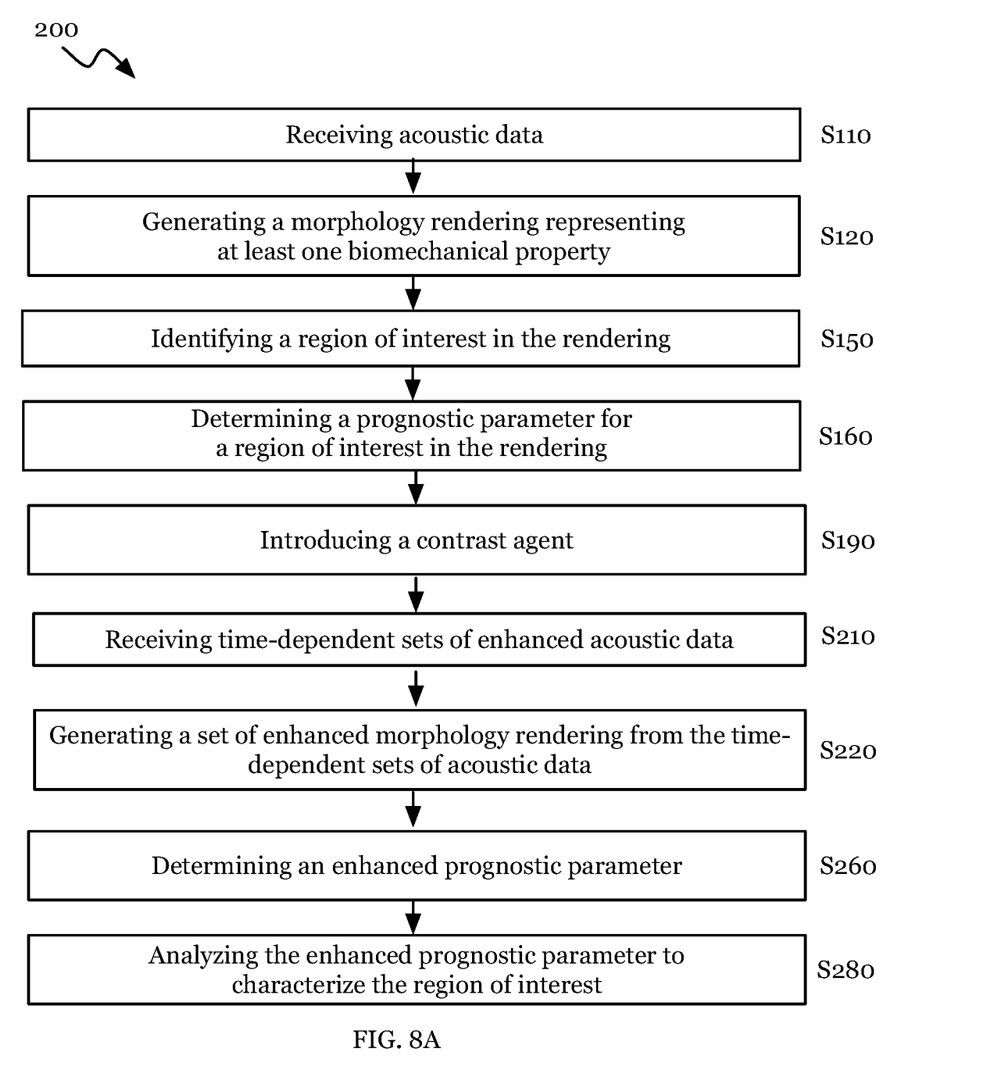
FIG. 8A and FIG. 8B are variations of the method of a second preferred embodiment.
Figure 8B:
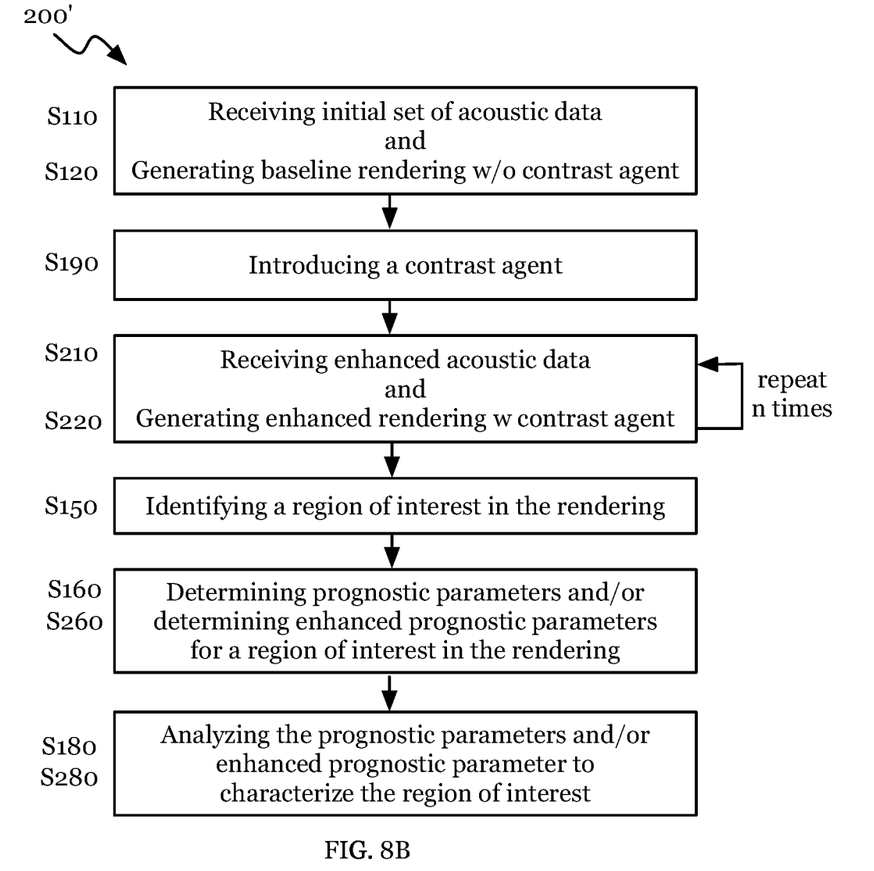

In a second preferred embodiment, as shown in FIG. 8A, the method 200 further includes introducing a contrast agent to the tissue S190, which functions to increase the number of available prognostic parameters and potentially increase accuracy of characterization. In this embodiment, the method preferably further includes: receiving time-dependent sets of enhanced acoustic data S210 after introducing the contrast agent into the tissue; generating a set of enhanced morphology renderings S220 from the time-dependent sets of enhanced acoustic data; determining an enhanced prognostic parameter S260 based on the set of enhanced renderings; and analyzing the enhanced prognostic parameter S280. These steps and the steps of the first preferred embodiment of the method may be performed in any suitable order. For instance, as shown in FIG. 8B, gathering unenhanced and enhanced acoustic data and generating unenhanced and enhanced renderings may be performed before determining and analyzing prognostic parameters and enhanced prognostic parameters.

Introducing a contrast agent the tissue S190 may include introducing into the tissue Definity, Optison, and/or any contrast agent suitable for medical diagnostics. The contrast agent is preferably introduced after a first acoustic data set (without the contrast agent) is obtained, such that the first acoustic data set forms a baseline from which a baseline morphology rendering may be generated. In other words, some or all of the steps of the method of the first preferred embodiment may be initially performed before introducing the contrast agent. Alternatively, in the second embodiment of the method, the step of receiving an acoustic data set prior to introducing the contrast agent may be omitted, such that no baseline rendering without the effects of the contrast agent is formed. The contrast agent may be introduced intravenously (or in any suitable manner) at the beginning of scanning, as known by one skilled in the art, to allow circulation throughout the volume of tissue. The introduction of a contrast agent preferably further enhances the biomechanical differences between a region of interest and its surrounding tissue as they appear in the renderings based on the enhanced acoustic data. In particular, the contrast agent may be used to increase relative acoustic reflectivity and acoustic attenuation, and decreases relative acoustic speed within a region of interest.

Receiving time-dependent sets of enhanced acoustic data S210 functions to obtain data that provides a "snapshot" at various times during the interaction of acoustic waves and the tissue with the contrast agent. Generating an enhanced morphology rendering S220 from the enhanced acoustic data functions to provide one or more chronological renderings that represent time-dependent biomechanical properties. Obtaining time-dependent sets of enhanced acoustic data S210 and generating an enhanced morphology rendering S220 are preferably similar to obtaining acoustic data S110 and generating a morphology rendering S120 of the first preferred embodiment. The ring transducer, or any other suitable transducer, may make repeated passes along the tissue to obtain data at specified time intervals, allowing the generation of a morphology rendering corresponding to various times after the introduction of the contrast agent. For instance, the series of enhanced renderings may include renderings of one or more biomechanical properties corresponding to t=0 seconds (when the contrast agent is introduced), and approximately every 30 seconds up to, for example, 420 seconds. However, the renderings may correspond any suitable intervals of time and length of time after introduction of the contrast agent, including only one point in time after introduction of the contrast agent (renderings corresponding to a singular scan, rather than repeated scans over intervals of time).

Figure 9:
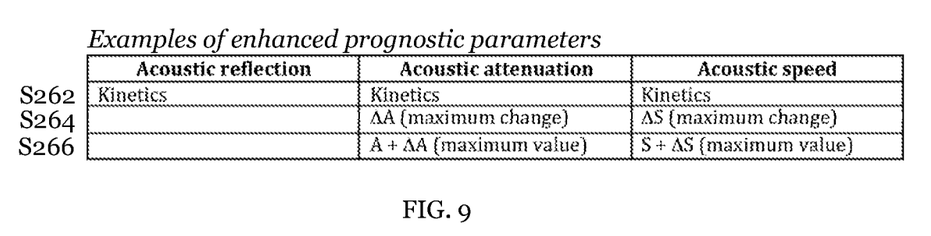
FIG. 9 is a table summarizing the step of determining an enhanced prognostic parameter in the method of a second preferred embodiment.

Determining an enhanced prognostic parameter S260 based on the set of enhanced renderings functions to establish a measure of the changes of biomechanical properties as a result of the introduction of a contrast agent. One or more enhanced prognostic parameters, similar to the prognostic parameters of the method of the first embodiment (or prior to introduction of the contrast agent) may include: an acoustic reflection parameter representing the acoustic reflectivity, an acoustic attenuation parameter representing the acoustic attenuation, and/or an acoustic speed parameter representing the acoustic speed in the region of interest after the contrast agent is introduced into the tissue. As shown in FIG. 9, determining one or more enhanced prognostic parameters may additionally and/or alternatively include: determining the kinetics of flow of the contrast agent S262 across the time-dependent set of enhanced renderings ("wash-in, wash-out" flow as visualized, for example, in the acoustic reflection, acoustic attenuation, and/or acoustic speed renderings), determining the maximum change in value of a biomechanical property S264 in the region of interest (e.g., volume averaged values of acoustic attenuation or acoustic speed) between the baseline rendering and among the set of enhanced renderings, and/or determining the maximum value of a biomechanical property in the region of interest S266 (e.g., volume averaged value of acoustic attenuation or acoustic speed) in the set of enhanced renderings. However, the enhanced prognostic parameter may be any of the quantitative or qualitative prognostic parameters as described in the method of the first embodiment, or any suitable enhanced prognostic parameter.

Analyzing the enhanced prognostic parameter S280 functions to evaluate the one or more enhanced prognostic parameters to further characterize the region of interest, such as for distinguishing malignant tissue from benign tissue or other characterizations. Analyzing the enhanced prognostic parameter S280 is preferably similar to analyzing the prognostic parameter S180 as in the method of the first preferred embodiment. For example, analyzing the enhanced prognostic parameter S280 may include navigating a decision tree with enhanced prognostic parameters, and/or inputting the enhanced prognostic parameter into a predictive model. The decision tree and predictive model using the enhanced prognostic parameters may have thresholds and specific algorithms different from or similar to that of the first embodiment with non-enhanced prognostic parameters. However, analyzing the enhanced prognostic parameter S280 may include any suitable analysis.

As a person skilled in the art will recognize from the previous detailed description and from the figures and claims, modifications and changes can be made to the preferred embodiments of the invention without departing from the scope of this invention defined in the following claims.

We claim:

1. A system for characterizing a tissue volume of a patient, comprising:
a processor configured with instructions to:
receive an acoustic data set derived from acoustic waves detected by a transducer;
generate two or more renderings of the tissue volume from the acoustic data set, wherein the two or more renderings comprise a first rendering representing a distribution of acoustic reflection within the tissue volume and a second rendering representing a distribution of acoustic attenuation or a distribution of acoustic speed within the tissue volume:
generate a merged rendering of the tissue volume from at least the first rendering and the second rendering;
identify a region of interest from the merged rendering;
determine a qualitative prognostic parameter, wherein the qualitative prognostic parameter characterizes a margin of the region of interest identified from the merged rendering according to an integer scale;
determine a quantitative prognostic parameter for the region of interest identified from the second rendering, wherein the at least one quantitative prognostic parameter comprises an attenuation value or a speed value; and
output an analysis of the region of interest derived at least from the quantitative prognostic parameter and the qualitative prognostic parameter, wherein the analysis is indicative of a presence of cancer within the tissue volume.

2. The system of claim 1, wherein the processor is configured to identify an outline of the region of interest from the merged rendering.

3. The system of claim 1, wherein the processor is configured to identify an outline of the region of interest in the first rendering or the second rendering and replicate the outline of the region of interest in the merged rendering to identify the outline of the region of interest from the merged rendering.

4. The system of claim 1, wherein the processor is configured to characterize the region of interest as at least one of: a cancerous tumor, a fibroadenoma, a cyst, a non-specific benign mass, and an unidentifiable mass.

5. The system of claim 1, wherein the processor is configured to determine a volume average value of attenuation or a volume average value of speed.

6. The system of claim 1, wherein the first rendering and the second rendering comprise two-dimensional images.

7. The system of claim 1, wherein the first rendering and the second rendering comprise three-dimensional images.

8. The system of claim 1, wherein the merged rendering is a two-dimensional rendering.

9. The system of claim 1, wherein the merged rendering is a three-dimensional rendering.

10. The system of claim 1, further comprising the transducer, wherein the transducer comprises a receiver configured to detect the acoustic waves from the tissue volume.

11. The system of claim 10, wherein the transducer comprises a plurality of receivers configured to detect the acoustic waves from the tissue volume.

12. The system of claim 1, further comprising the transducer, wherein the transducer comprises a transmitter configured to emit the acoustic waves towards the tissue volume.

13. The system of claim 12, wherein the transducer comprises a plurality of transmitters configured to emit the acoustic waves towards the tissue volume.

14. The system of claim 1, further comprising the transducer, wherein the transducer comprises a ring-shaped transducer configured to surround the tissue volume.

15. The system of claim 1, wherein the processor is configured to navigate a decision tree that compares at least one of the quantitative prognostic parameter and the qualitative prognostic parameter of the region of interest to a threshold.

16. The system of claim 1, further comprising a display in communication with the processor, wherein the display is configured to display rendered information derived from the analysis.

17. The system of claim 1, further comprising an imaging tank configured to receive the tissue volume.

18. The system of claim 4, wherein the analysis of the region of interest comprises characterizing the region of interest as benign if the qualitative prognostic parameter is below a first threshold value on the integer scale and the quantitative prognostic parameter is below a second threshold value.

19. The system of claim 4, wherein the analysis of the region of interest comprises characterizing the region of interest as cancerous if the qualitative prognostic parameter is above a first threshold value on the integer scale and the quantitative prognostic parameter is above a second threshold value.

20. The system of claim 1, wherein the quantitative prognostic parameter is derived from multiple patient exams performed at different intervals of time.

* * * * *

UNITED STATES PATENT AND TRADEMARK OFFICE
CERTIFICATE OF CORRECTION

| | |
|---|---|
| PATENT NO. | : 11,399,798 B2 |
| APPLICATION NO. | : 16/217275 |
| DATED | : August 2, 2022 |
| INVENTOR(S) | : Nebojsa Duric and Peter John Littrup |

It is certified that error appears in the above-identified patent and that said Letters Patent is hereby corrected as shown below:

In the Specification

In Column 1, Line 17, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Sixth Day of August, 2024

Katherine Kelly Vidal
*Director of the United States Patent and Trademark Office*